United States Patent [19]
Bignami et al.

[11] Patent Number: 5,364,531
[45] Date of Patent: Nov. 15, 1994

[54] PROCESS FOR AFFINITY PURIFICATION BY IMMUNOADSORPTION IN NON-AQUEOUS SOLVENT

[75] Inventors: Gary S. Bignami, Waialua; Paul G. Grothaus, Mililani, both of Hi.

[73] Assignee: Hawaii Biotechnology Group, Inc., Aiea, Hi.

[21] Appl. No.: 974,338

[22] Filed: Nov. 10, 1992

Related U.S. Application Data

[63] Continuation of Ser. No. 532,631, Jun. 1, 1990, abandoned.

[51] Int. Cl.$^5$ ............................................. B01D 15/08
[52] U.S. Cl. .................................... 210/635; 210/656; 210/198.2; 530/413; 530/417
[58] Field of Search ...................... 210/635, 656, 198.2, 210/502.1; 436/161; 530/413, 417

[56] References Cited

U.S. PATENT DOCUMENTS

| | | | |
|---|---|---|---|
| 4,000,098 | 12/1976 | Hofstee | 530/413 |
| 4,169,790 | 10/1979 | Pretorius | 210/656 |
| 4,485,017 | 11/1984 | Tan | 530/413 |
| 4,608,347 | 8/1986 | Bernstam | 436/175 |
| 4,740,306 | 4/1988 | Litwack | 210/198.2 |
| 4,742,000 | 5/1988 | Greene | 530/413 |
| 4,774,190 | 9/1988 | Weiss | 210/656 |
| 4,818,684 | 4/1989 | Edelman | 530/413 |
| 4,913,902 | 4/1990 | Kilpatrick | 530/413 |
| 4,957,620 | 9/1990 | Cussler | 210/635 |
| 5,055,390 | 10/1991 | Weaver | 435/182 |

OTHER PUBLICATIONS

Mikes Laboratory Handbook of Chromatographic and Allied Methods, John Wiley & Sons, New York, 1979, pp. 385–387.
Durfor, et al., "Antibody Catalysis In Reverse Micelles", *J. Am. Chem. Soc.*, 110:8714–8716, (1988).
Zaks & Klibanov, "Enzymatic Catalysis In Non-Aqueous Solvents", *Journal of Biological Chemistry*, 263:3194–3201, (1988).
Ron Dagani, "Enzyme Active In Hot Organic Media", *Chemical and Engineering News*, Jul. 2, 1984, p. 23.
Zaks & Kilibanov, "Enzymatic Catalysis in Organic Media at 100 C", Science 224: 1249–1251 (1984).
Russell & Kilbanov, "Inhibitor-Induced Enzyme Activation In Organic Solvents", *The Journal of Biological Chemistry*, 263:11624–11626, (1988).
Kazandjian, et al., "Enzymatic Analyses in Organic Solvents", 28:417–421, *Biotechnology and Bioengineering* (1986).
Kazandjian and Klibanov, "Regioselective Oxidation of Phenols Catalyzed by Polyphenol Oxidase in Chloroform", 107:5448–5450 (1985).
Klibanov, "Enzymes that Work in Organic Solvents", *Chemtech*, Jun.:354–359, (1986).
Zaks and Klibanov, "Substrate Specificity of Enzymes in Organic Solvents vs. Water is Reversed", *J. Am. Chem. Soc.* 108:2767–2768 (1986).
Klibanov, "Enzymatic Catalysys in Anhydrous Organic Solvents", *Trends in Biochemical Science*, 14:141–144, (1989).
Russell, et al., "Antibody-Antigen Binding In Organic Solvents", *Biochemical and Biophysical Research Communications*, 158:80–85, (1989).
Kabanov, et al., "A New Way in Homogeneous Immunoassay:Reversed Micellar Systems as a Medium for Analysis", *Anal. Biochem.*, 181:145–148, (1989).
Chem Abstract 112(13):114692 P (1989).

*Primary Examiner*—Ernest G. Therkorn
*Attorney, Agent, or Firm*—Barbara Rae-Venter; Bertram Rowland

[57] ABSTRACT

Immunoaffinity purifications are performed using non-aqueous media, desirably, a small amount of an aqueous buffered medium, and, optionally, a surfactant. Hydrophobic ligands can be extracted from samples, immunoaffinity purified and eluted to provide a substantially pure product.

13 Claims, No Drawings

PROCESS FOR AFFINITY PURIFICATION BY IMMUNOADSORPTION IN NON-AQUEOUS SOLVENT

CROSS REFERENCE TO RELATED APPLICATIONS

This application is a continuation of U.S. application Ser. No. 07/532,631, filed Jun. 1, 1990, now abandoned.

TECHNICAL FIELD

The field of this invention is the purification/separation or removal of a ligand of interest from a complex mixture in a non-aqueous solvent medium, by the use of a specific binding protein immobilized to a solid phase.

BACKGROUND

The use of specific receptors for immunoaffinity purification, or immunoaffinity purification of such receptors from complex mixtures has found extensive applications, particularly in the biopharmaceutical field. In this field, one has been interested in purifying a wide variety of biological compounds from the media in which they are present. These media may be extracts of naturally occurring prokaryotic or eukaryotic cells or supernatants from artificially cultured cells that contain secreted products. These compounds are for the most part water soluble at the concentration of interest. Purification methods are normally based on the specific recognition by a protein immobilized on a solid base, of a protein or non-proteinaceous analyte, where the binding of the protein receptor and its complementary ligand normally occurs in an aqueous medium.

In many situations, there may be an interest in separating ligands from non-aqueous media. One may wish to extract a hydrophobic compound from a specimen such as soil, fat, oil, or the like, where it would be desirable to retain the extracted compound in a non-aqueous medium. There is, therefore, substantial interest in being able to develop specific immunoadsorption affinity purification methods which allow the use of non-aqueous solvents.

RELEVANT LITERATURE

Durfor et al., *J.A.C.S.* (1988), 110:8714–8716, described antibody catalysis in reverse micelles. Zaks and Klibanov, *J. Biol. Chem.* (1988), 263:3194–3201, describe enzymatic catalysis in non-aqueous solvents. See also Chemical and Engineering News, Jul. 2, 1984, page 23. Zaks and Klibanov, *Science* (1984), 224:1229–1231, describe enzymatic catalysis in organic media at 100° C. Russell and Klibanov, *J. Biol. Chem.* (1988), 263:11624–11626, describe inhibitor-induced enzyme activation in organic solvents. Kazandjian et al., *Biotechnology and Bioengineering*, (1986), 23:417–421, describe enzymatic analyses in organic solvents. Kazandjian and Klibanov, *J.A.C.S.* (1985), 107:5448–5450, describe regioselective oxidation of phenols catalyzed by polyphenol oxidase in chloroform. Klibanov, Enzymes That Work In Organic Solvents, *Chemtech*, (June, 1986), 354–359, discusses enzymatic catalysis in organic solvents. Zaks and Klibanov, *J.A.C.S.* (1986), 108:2767–2768, compare substrate specificity of enzymes in organic solvents in relation to water. Klibanov, *TIBS*, (1989), 14:141–144, describes enzymatic catalysis in anhydrous organic solvents. Russell et al., *Biochem. and Biophys. Res. Comm.* (1989), 158:80–85, describe antibody-antigen binding in organic solvents. Kabanov, et al., *Anal. Biochem.* (1989), 181:145–148, describe homogeneous immunoassay in reversed micelles of AOT in octane.

SUMMARY OF THE INVENTION

Affinity purification is provided by immunoadsorption using solid phase antibody immunoadsorbents and non-aqueous media/solvents, where the media/solvents may comprise a small amount of an aqueous buffer and a surfactant. Various solid phase supports, solvent systems, and protocols may be employed to immunopurify a compound of interest.

DESCRIPTION OF THE SPECIFIC EMBODIMENTS

Novel methods for specific antibody-mediated affinity purification by immunoadsorption are provided employing organic solvents, particularly hydrocarbons, as the sample, washing and eluting media. The sample may be pretreated as desired, and dispersed into the solvent sample medium. The solvent medium may then be combined with the complementary solid-phase specific antibody and the mixture allowed to incubate for specific binding to occur between the solid-phase antibody and its complementary ligand. The ligand may then be eluted from the solid-phase specific antibody by treatment with a suitable organic solvent eluting agent.

Antibody-mediated non-aqueous immunoaffinity purification methods may be used for a variety of useful applications. In the analysis of hydrophobic compounds, non-aqueous immunoaffinity purification can be exploited as a pretreatment step, to afford a less complex sample matrix, prior to subsequent instrumental analysis, e.g., HPLC, UV, visible, or IR spectroscopy, refractive index, fluorimetry, electrochemical detection, NMR, GC-MS, and the like. Also, non-aqueous immunoaffinity purification may provide an analytical method, in combination with an internal standard, e.g., radiolabeled or fluorochrome labeled tracer, and a method for detection of the eluted ligand, e.g., UV, visible, or IR spectroscopy, refractive index, fluorimetry, electrochemical detection, and the like. Non-aqueous immunoaffinity purification can be exploited as a preparative method for isolation of purified ligand. For preparative purposes, the amount of immobilized proteinaceous receptor may be increased to provide the required ligand-binding capacity. Also, replicate solid-phase receptor units, where the unit may be a column, cartridge, or other vessel containing solid-phase receptor, may be alternately incubated with sample matrix or eluted with eluting solvent. Regeneration of the binding-capacity of the solid-phase protein receptor following elution may permit multiple application and elution cycles of ligand effecting a continuous mode of operation. Such preparative techniques could be useful for the isolation of a desired ligand from fine chemical, pharmaceutical, agricultural chemical, industrial waste process streams, and the like.

The sample may be any industrial or biological material in which a ligand is present, particularly where the ligand is a hydrophobic compound. Biological samples may be animal or plant tissue, physiological fluid, feces, bile, fat or plasma samples. Industrial samples may include soil samples and industrial organic chemicals, whether they be final products, process intermediates or wastes from the pharmaceutical, pesticide, pulp and paper, oil, or similar industries. In many plant and animal tissues, the presence of various organic compounds may be of interest. For example, aflatoxin in peanuts, pesticides in animal fat, or the like may be of interest. In soils, particularly soils associated with industry, such as agriculture, chemical processing, synthesis of organic compounds, the electronic industry, or the like, various organic compounds may be introduced or seep into the soil. These compounds include but are not limited to pesticides e.g. haloaromatic or aliphatic fungicides, herbicides, insecticides, etc., processing compounds in electronics, etc. The determination of the presence of these compounds can be important in determining whether waste storage is leaking, violations of rules and regulations concerning disposal of compounds, determination of hazardous materials in chemical waste drums, quality control of bulk organic chemicals and process intermediates, or the like. In addition, there are a number of lipid soluble compounds in physiological fluids or tissues which are of interest. These include endogenous compounds, e.g. steroids, bile acids, Vitamin A and derivatives, etc., toxic compounds, therapeutic and illicit drugs, particularly where such compounds may be stored in fatty tissue. Pollutants of particular interest include such pollutants as the dibenzodioxins or -furans, e.g. dibenzo-p-dioxin, dibenzo-p-furan, 2,3,7,8-tetrachloro-dibenzo-p-dioxin or 2,3,7,8-tetrachloro-dibenzo-p-furan.

With many of these samples, it may be necessary desirable to extract lipid soluble material into an organic solvent. Thus, the extract will provide the sample to be used. For extraction, the same solvent as used for sample incubation is not required, so long as the extracting solvent is substantially miscible with the assay medium in the amounts used. Thus, various solvents may be used, which have different hydrophilicity than the solvents used in the incubation medium. In some instances, the compound of interest may be dispersed in an aqueous medium due to solubilizing compounds such as proteins or detergents. In this instance, so long as the sample is small and can be dispersed in the hydrophobic medium without separation, the sample may be used directly.

In carrying out the separation, the sample containing the compound of interest will initially be combined with the incubation medium. The sample medium may be hydrocarbon, aliphatic or aromatic halohydrocarbon, oxy, e.g. alkanolic or phenolic, or ether, oxo e.g., ketone, carboxy e.g. amide or ester, etc., or combinations thereof. The incubation medium has a major portion of an organic solvent, a liquid at the temperature of the separation, preferably combined with not more than about 2% by volume, usually not more than about 0.2%, and optionally, at least about 0.05%, by volume of an aqueous buffer and up to about 5 mM of surfactant, e.g., anionic, non-ionic or cationic, particularly anionic. The surfactant, while not essential for obtaining specific binding as compared to non-specific binding is particularly desirable, generally in at least about 0.5 mM.

For the most part, the solvents will be hydrocarbons or halohydrocarbons, aliphatic and alicyclic, where the halohydrocarbons have halogen of atomic numbers 9 or 17, although 0-2 heteroatoms, e.g., O, N. or S, may be present where the carbon/heteroatom ratio is at least 4:1. Desirably the solvents are aliphatic hydrocarbons of from 5 to 18 carbon atoms, particularly of from 6 to 16 carbon atoms, particularly straight chain. The halohydrocarbons will generally be of from about 2 to 6 carbon atoms, more usually from 2 to 4 carbon atoms, generally containing at least one halogen and up to perhalo. Illustrative compounds include hexane, heptane, octane, decane, dodecane, pentadecane, hexadecane, 2,6-dimethyloctane, toluene, cumene, cyclooctane, chloroform, dichloromethane, etc.

The solvent will usually dissolve less than 10% v/v of water. The incubation medium will normally contain not more than about 5%, usually not more than about 2%, preferably not more than about 0.2% by volume of a buffer solution, at a pH from about 5 to 10, more usually 6 to 9. For the most part, the solvents which dissolve less than about 0.2% v/v of the buffer medium will be saturated with the buffer medium. Generally the buffer will be present in from about 10 to 200 mM, usually 50 to 150 mM, and various buffers may be used, such as phosphate, phosphate buffered saline, carbonate, Tris, MOPS, HEPES, or the like. Of particular interest are inorganic buffers. Salts may be present, other than the buffer, e.g. NaCl, generally ranging in amount from about 0 to 1.0% (w/v).

The third ingredient of the medium may be a surfactant, particularly an anionic surfactant. The anionic surfactants may be aromatic or aliphatic, particularly aliphatic, normally a salt of an organic acid or ester, including carboxylates, sulfonates, sulfates, phosphonates, cationic surfactants include CTAB; while nonionic surfactants include polyoxyethylene glycol ethers and esters. The surfactant may be an individual surfactant or a combination of compatible surfactants. Other functionalities may be present in the surfactant, particularly oxygen containing functionalities, such as ethers, esters, carbonyls, hydroxyl, and the like. Of particular interest is the diester of sulfosuccinate where the alkyl groups may be of 6 to 12 carbon atoms, particularly 8 carbon atoms. The concentration of the surfactant will vary depending upon the particular surfactant, generally not exceeding about 5 mM, preferably being from about 0.02 to 3 mM, more preferably from about 0.1 to 2 mM. The surfactant may serve to minimize non-specific binding.

The dilution of the sample into the incubation medium will depend upon the concentration of the compound of interest in the sample, the nature of the medium containing the sample, and the like. The extracted sample may provide the incubation medium, but the sample may be less than 50 volume % of the incubation medium, and may be as small as 1% or less of the incubation medium.

The proteinaceous receptor will usually be an antibody or fragment thereof, including the various isotypes, e.g., murine IgG$_1$, IgG$_{2a}$, IgG$_{2b}$, IgG$_3$, IgM, IgA, IgD and IgE, fragments such as F(ab')$_2$, Fab', Fv, etc.

Various protocols may be used for separation of the compound of interest:

1) batch configuration: Antibody immobilized on a solid phase, e.g., Pyrex ® glass beads, controlled pore glass, Nylon ® rods, and the like, may be added to a vessel for incubation with the ligand containing sample, or visa versa. Alternatively, the vessel itself may provide the solid phase substrate for immobilization of antibody. In such cases, after contact with the substrate, the ligand-containing sample in incubation medium will be removed, through aspiration, pouring, or the like, prior to washing with incubation incubator medium to reduce non-specific binding, and subsequent elution of the specifically-bound ligand with eluting solvent.

2) column or cartridge configuration: Antibody immobilized on a solid phase, e.g., Pyrex® glass beads, controlled pore glass, glass wool, agarose or cross-linked agarose, polyacrylamide or cross-linked dextran beads, fiberglass, Nylon®, Teflon®, or other solvent resistant membranes and the like, which may be contained in a solvent resistant unit such as a column, cartridge, or the like. The configuration of such solid-phase units will allow sample addition through an inlet port for a binding incubation, followed by sample removal through an outlet port. Similarly, elution may be effected, following a ligand-binding incubation through addition of elution solvent via the inlet port and removal through the outlet port.

The ligand bound to the support may be removed by elution, using any convenient organic solvent eluent, by itself or in combination with elevated temperatures.

The following examples are offered by way of illustration and not by way of limitation.

EXPERIMENTAL

Materials and Methods
  Abbreviations:
    BSA=Bovine Serum Albumin
    PBS=0.01M Sodium phosphate, 0.15M NaCl (pH 7.0)
    PBS/BSA=PBS+1% BSA
  Materials:
    Reagents employed were purchased from the following suppliers:
    Purified normal rabbit IgG (Pierce)
    Protein G columns (Genex, GammaBind-G)
    Rabbit IgG standards (Sigma)
    [$^3$H] Estradiol (Amersham), 94 Ci/mmol
    [$^3$H] Progesterone (Amersham), 85 Ci/mmol
    Ecolume liquid scintillation cocktail (ICN)
    Pyrex beads, 3 mm diam. (Baxter)
    Karl Fischer reagent (Fisher Scientific)
    Solvents, anhydrous Grade (Aldrich Chemical Co.)
    AOT-dioctyl sulfosuccinate sodium salt (Sigma)

Antibody Preparation and Quality Control a. Preparation of purified rabbit IgG fractions from whole sera.

Protein G columns containing 1.0 ml recombinant protein G covalently immobilized on Sepharose 4B were used to isolate the IgG fraction from rabbit sera by affinity chromatography. Protein G chromatography was performed as follows: Serum samples were clarified by centrifugation at 16,000×g for 15 min, and diluted 1:1 with PBS loading buffer. Protein G columns were equilibrated with 10 ml PBS and 1.0 ml of diluted serum was then loaded onto the column. Unbound protein was washed from the column with PBS at a flow rate of 1.0 ml/min, using a peristaltic pump. Eluted protein was monitored by UV absorbance at 280 nm ($A_{280}$). When the ($A_{280}$) had returned to baseline value, bound IgG was eluted with 2 ml of 0.5M ammonium acetate (pH 3.0). IgG fractions were collected into tubes containing equal volumes of 1.5M Tris-HCl (pH 8.8) in order to allow rapid neutralization of the elution buffer pH. Fractions containing IgG were combined and dialyzed extensively against PBS. Immunoglobulin concentration was estimated by UV spectroscopy at 278 nm using an extinction coefficient for rabbit IgG of 1.4 for a 1 mg/ml solution.

Purity of rabbit IgG fractions was assessed by SDS-PAGE [Laemmli, Nature (1970), 277:680] visualized by the silver staining method [Hukeshoven and Dernick, Electrophoresis (1985), 6:103]. Protein G affinity chromatography resulted in a purification estimated to be equal to or greater than 90% when compared to rabbit IgG standards.

Protein G purified IgG fractions were checked for antigen binding capacity by a precipitation RIA as described below. Binding capacity of the IgG fractions was retained following chromatography.

b. Precipitation RIA Procedure:

0.36 ml of antibody preparation serially diluted in PBS+1% BSA and 0.04 ml radiolabeled antigen (0.1 μCi) were combined and mixed, then incubated for 1 hr at 37° C. in a water bath. Then 0.1 ml of a 0.1M EDTA, (ethylenediamine tetraacetic acid) in water solution pH 7.0 and 0.2 ml of a 2% (v/v) normal rabbit serum in PBS+1% BSA solution were added to each sample and mixed. Then 0.1 ml of an optimally diluted goat anti-rabbit IgG and 0.5 ml of a 6% (w/v) polyethylene glycol 6000 in PBS+1% BSA solution was added to each sample, mixed, and incubated for 5 min at ambient room temperature. Each sample was then centrifuged at 15,000×g for 15 min at 4° C. The pelleted material was washed by centrifugation 3 times with 0.5 ml PBS+1% BSA and the precipitate solubilized with 0.3 ml of 0.1N NaOH. 0.15 ml of the dissolved pellet was then added to 3 ml scintillation cocktail and the radioactivity quantified using standard liquid scintillation counting techniques.

c. Immobilization of Rabbit IgG to Solid Phase.

Pyrex TM glass beads were utilized as the solid phase for immobilization of the antibody-containing IgG fraction of rabbit serum (See U.S. patent application Ser. No. 425,759, filed Oct. 23, 1989). Pyrex beads were cleaned by treatment with 5% nitric acid at 100° C. for 1 hour, followed by extensive rinsing with distilled water and acetone. The glass surface of the Pyrex beads was then activated by heating at 500° C. for 5 hours, followed by cooling to room temperature in a desiccator [Hamaguchi et al., *J. Biochem.* (1976), 80:89–898]. The beads were then immersed in a solution of 2% 3-aminopropyltriethoxysilane (APTES) in acetone, and allowed to stand at 45° C. for 24 hr. After cooling to room temperature, the aminated glass beads were washed repeatedly with acetone and stored in a desiccator until used for antibody immobilization. Antibodies were immobilized on the beads using Robinson's modification [Robinson et al., Biochem. Biophys. ACTA, (1971), 242:659–661] of the general method of Weetall [Meth. Enzymol. (1976), 44:137–147]. Thirty-six aminated Pyrex beads were treated with 8% aqueous glutaraldehyde for 30 min at room temperature. The beads were thoroughly washed with distilled water and suspended in 2 ml of PBS containing 720 μg of purified IgG and allowed to stand at 4° C. for 24 hr. The beads were then washed with PBS and resuspended in 2 ml of PBS containing 720 μg of normal rabbit IgG. After standing at room temperature for 2 hr, the beads were exhaustively washed with PBS. After decanting off all liquid, the beads were frozen and lyophilized.

d. Storage.

Antibodies immobilized on Pyrex beads were stored in a vacuum desiccator over Drierite at 4° C. until required for use. The desiccator containing the beads was allowed to equilibrate to room temperature before the vacuum was released and beads removed.

Solvents a. Purity.

Organic solvents were anhydrous grade, certified to contain <0.0005% water. The water content of all solvents was checked by Karl Fischer titration and found to be below the level of detection of this method.

b. Karl Fischer Titration.

Fischer titrations were performed with an Aquametry II apparatus from Lab Industries. Stabilized Karl Fischer reagent (KFR) and diluent were purchased from Fisher Scientific. The limit of detection was determined by the minimum buret reading (0.05 ml), the concentration of KFR and the sample aliquot (2 ml). The commercial KFR had a titer of 6.16 mg water per ml KFR. This was diluted to a titer of 1.61 mg water per ml KFR. Further dilutions gave irreproducible titration results. The limit of detection was 0.08 mg water (~0.002% [w/w] depending on the density of the solvent.

EXPERIMENTAL PROCEDURES AND RESULTS

Organic Phase Immunoaffinity Purification of Estradiol from a Mixture containing excess Progesterone.

Experiment 1

Pyrex beads coated with immobilized estradiol-specific IgG (Anti-Estradiol) or normal rabbit IgG (NRIgG) were incubated at 4° C. for 3 h in PBS, pH 7.0 saturated hexane containing 0.2 mM AOT with 0.94 p mol [$^3$H] Estradiol and 318 n mol [$^{14}$C] Progesterone, then washed three times with ice cold PBS pH 7.0 saturated hexane containing 0.2 mM AOT. Bound tracers were eluted at 22° C. for the specified time with 1 ml acetonitrile. Bound tracers were determined using standard scintillation counting techniques. The results presented in Table 1 show:

a) estradiol is bound specifically by immobilized anti-estradiol when compared to NRIgG.
b) progesterone is not bound specifically by anti-estradiol when compared to NRIgG binding.
c) estradiol bound to anti-estradiol can be eluted with acetonitrile.

TABLE 1

Organic Phase Immunoaffinity Enrichment of Estradiol in the Presence of Progesterone
% Added Material

| | % Bound at indicated time following elution treatment | | | % Eluted at indicated time | |
|---|---|---|---|---|---|
| | 0' | 5' | 15' | 5' | 15' |
| $^3$H estradiol | | | | | |
| NRIgG | 0.30[1] | 0.20 | 0.21 | 0.21[2] | 0.17 |
| Anti-estradiol | 0.81[1] | 0.43 | 0.21 | 2.05[2] | 1.49 |
| $^{14}$C progesterone | | | | | |
| NRIgG | 0.12[3] | 0.13 | 0.05 | 0.01[4] | 0.01 |
| Anti-estradiol | 0.14[3] | 0.07 | 0.04 | 0.09[4] | 0.00 |

[1] $0.01 < p \leq 0.025$
[2] $p \leq 0.0005$
[3] $0.1 < p \leq 0.375$
[4] $0.375 < p \leq 0.4$ Experiment 2

Pyrex beads coated with immobilized estradiol-specific IgG (Anti-Estradiol) or normal rabbit IgG (NRIgG) were incubated at 4° C. for 18 h in PBS pH 7.0 saturated hexane containing 0.2 mM AOT with 1.02 p mol [$^3$H] Estradiol and 3.5 n mol [$^{14}$C] Progesterone, then washed three times with ice cold PBS pH 7.0 saturated hexane containing 0.2 mM AOT. Bound tracers were eluted at 22° C. for 15 min. with 1 ml acetonitrile. Bound and eluted tracers were determined using standard scintillation counting techniques. The data presented in Table 2 clearly demonstrate:

a) estradiol is bound specifically by immobilized anti-estradiol when compared to binding of immobilized NRIgG.
b) the amount of progesterone bound to solid phase IgG is not dependent on anti-estradiol specificity.
c) estradiol bound to anti-estradiol can be eluted with acetonitrile.
d) the amount of estradiol bound to anti-estradiol increases in proportion to the amount of anti-estradiol present.
e) the amount of estradiol eluted from anti-estradiol increases in proportion to the amount of anti-estradiol present.
f) the amount of progesterone eluted from solid phase IgG is not dependent on anti-estradiol specificity.

TABLE 2

The Yield of Product Obtained by Organic Phase Immunoaffinity Enrichment is Proportional to the Amount of Ligand-specific Antibody
% Added Material

| | $^{14}$C Progesterone | | $^3$H Estradiol | |
|---|---|---|---|---|
| | Bound | Eluted | Bound | Eluted |
| NRIgG | | | | |
| 1 bead | 0.16[1] | 0.07[3] | 0.44[5] | 0.16[7] |
| 2 beads | 0.02[2] | 0.05[4] | 0.36[4] | 0.20[8] |
| Anti-estradiol | | | | |
| 1 bead | 0.06[1] | 0.06[3] | 2.00[5,9] | 2.35[7,10] |
| 2 beads | 0.07[2] | 0.12[4] | 3.30[6,9] | 5.49[8,10] |

[1] $0.025 < p \leq 0.05$
[2] $p > 0.4$
[3] $p > 0.4$
[4] $0.1 < p \leq 0.375$
[5] $0.0005 < p \leq 0.005$
[6] $p \leq 0.0005$
[7] $0.005 < p \leq 0.01$
[8] $p \leq 0.0005$
[9] $0.01 < p \leq 0.025$
[10] $0.0005 < p \leq 0.005$ Experiment 3

Pyrex beads coated with immobilized estradiol-specific IgG (Anti-Estradiol) or normal rabbit IgG (NRIgG) were incubated at 4° C. for 3 h in PBS pH 7.0 saturated hexane containing 0.2 mM AOT with 0.94 p mol [$^3$H] Estradiol and 318 n mol [$^{14}$C] Progesterone, then washed three times with ice cold PBS pH 7.0 saturated hexane containing 0.2 mM AOT. Bound tracers were eluted at 22° C. for 30 min. with 1 ml acetonitrile. The same beads were then incubated for a second time with 0.47 p mol [$^3$H] Estradiol and 159 n mol [$^{14}$C] Progesterone, at 4° C. for 50 h in PBS pH 7.0 saturated hexane containing 0.2 mM AOT. Following incubation, the beads were washed three times with ice cold PBS pH 7.0 saturated hexane containing 0.2 mM AOT. Bound tracers were determined using standard scintillation counting techniques. The results presented in Table 3 clearly show that following an initial incubation and elution with acetonitrile (as above), that immobilized antibody may be recycled, since:

a) estradiol is bound specifically by immobilized anti-estradiol when compared to binding of immobilized NRIgG.

b) the amount of progesterone bound to solid phase IgG is not dependent on anti-estradiol specificity.

The above results demonstrate that hydrophobic molecules may be isolated and purified using non-aqueous, particularly hydrophobic, media in conjunction with immunoaffinity separation substrates. In this manner hydrophobic analytes may be isolated from a wide variety of sources using non-aqueous extractants, purified with antibodies and then freed for isolation in pure form. The solvents may be readily removed to leave the product substantially free of contaminants.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

TABLE 3

Retention of Organic Phase Ligand Binding Capacity by Antibody Following Elution by Polar Solvent
% Added Material Bound

| | Post Elution | Reprobed × 50h |
|---|---|---|
| $^3$H Estradiol | | |
| NRIgG | 0.21[1,3] | 0.56[1,4] |
| Anti-estradiol | 0.21[2] | 1.4[2,3,4] |
| $^{14}$C Progesterone | | |
| NRIgG | 0.12 | 0.13 |
| Anti-estradiol | 0.14 | 0.12 |

[1] $0.025 < p \leq 0.05$
[2] $0.0005 < p \leq 0.005$
[3] $0.0005 < p \leq 0.005$
[4] $0.005 < p \leq 0.01$

What is claimed is:

1. A method for purifying hydrophobic substances comprising:
   contacting a sample mixture comprising a hydrophobic compound of interest and a hydrophobic non-aqueous solvent selected from the group consisting of aliphatic hydrocarbons of from 5 to 18 carbon atoms and halohydrocarbons of from 2 to 6 carbon atoms and capable of dissolving less than 10% v/v water, wherein said sample mixture optionally comprises either (i) an amount and composition of aqueous medium capable of either (i) an amount and composition of aqueous medium capable of dispersion in said hydrophobic non-aqueous solvent or (ii) a solvent substantially miscible with said hydrophobic non-aqueous solvent, with a solid-phase bound protein receptor for said compound of interest, whereby said compound of interest binds specifically to said receptor;
   separating said solid-phase from said sample mixture; and
   releasing said compound of interest from said solid-phase bound receptor.

2. A method according to claim 1, wherein said releasing substantially regenerates the binding capacity of said receptor.

3. A method for purifying hydrophobic substances comprising:
   contacting a sample mixture comprising a hydrophobic compound of interest, a hydrophobic non-aqueous solvent selected from the group consisting of aliphatic hydrocarbons of from 5 to 18 carbon atoms and halohydrocarbons of from 2 to 6 carbon atoms and capable of dissolving less than 10 volume percent water, less than two volume percent of an aqueous buffer solution at a pH of from about 5 to 10, and less than about 5 mM of a surfactant, wherein said aqueous buffer solution is either (i) of an amount and composition capable of dispersion in said hydrophobic non-aqueous solvent, or (ii) a solvent substantially miscible with said hydrophobic non-aqueous solvent, with a solid-phase bound protein receptor for said compound of interest, whereby said compound of interest becomes specifically bound to said receptor;
   separating said solid-phase from said sample mixture; and
   releasing said compound of interest from said solid-phase bound receptor.

4. A method according to claim 3, wherein said surfactant is an anionic organic surfactant.

5. A method according to claim 4, wherein said surfactant is a sulfonate carboxylate ester.

6. A method according to claim 3, wherein said solvent is a hydrocarbon or halohydrocarbon or combination thereof.

7. A method according to claim 3, wherein said solid-phase is heat and chemical resistant glass, controlled pore glass, glass wood, cross-linked agerose, polyacrylamide or cross-linked dextran beads, fiberglass, nylon, teflon or other solvent resistant membrane.

8. A method according to claim 3, wherein said compound of interest is asteroid.

9. A method for purifying hydrophobic substances comprising:
   contacting a single phase sample mixture a hydrophobic compound of interest, a solvent selected from the group consisting of aliphatic hydrocarbons of from 5 to 18 carbon atoms and halohydrocarbons of from 2 to 6 carbon atoms, less than two volume percent of an aqueous buffer solution at a pH of from about 5 to 10 and a buffer concentration in the range of 10 to 200 mM, and less than about 5 mM of a surfactant, wherein said aqueous buffer solution is of an amount and composition which is capable of dispersion in said solvent with a solid-phase bound monoclonal antibody specific for said compound of interest, whereby said compound of interest binds specifically to said antibody;
   separating said solid-phase from said sample mixture; and
   releasing said compound of interest from said solid-phase bound antibody.

10. A method according to claim 9, including the additional step of dissolving said compound of interest into said solvent from a sample.

11. A method according to claim 10, wherein said sample is a physiological fluid.

12. A method according to claim 9, wherein said aqueous buffer solution is phosphate buffered saline.

13. A method for purifying hydrophobic substances, said method comprising:
   contacting a sample mixture comprising a hydrophobic compound of interest, a hydrophobic non-aqueous solvent, selected from the group consisting of aliphatic hydrocarbons of from 5 to 18 carbon atoms and halohydrocarbons of from 2 to 6 carbon atoms, wherein said sample mixture optionally comprises either (i) an amount and composition of aqueous medium capable of dispersion in said hydrophobic non-aqueous solvent or (ii) a solvent substantially miscible with said hydrophobic non-aqueous solvent, with a solid-phase bound protein receptor for said compound of interest, whereby said compound of interest binds specifically to said receptor;

separating said solid-phase from said sample mixture; and releasing said compound of interest from said solid-phase bound receptor by elution with a solvent which is less hydrophobic than said hydrophobic non-aqueous solvent.

* * * * *